US00PP21583P3

(12) United States Plant Patent

Olesen et al.

(10) Patent No.: US PP21,583 P3

(45) Date of Patent: Dec. 21, 2010

(54) *CLEMATIS* PLANT NAMED 'EVIPO016'

(50) Latin Name: *Clematis viticella*
Varietal Denomination: Evipo016

(75) Inventors: Mogens N. Olesen, Fredensborg (DK); Raymond J. Evison, Domarie Vineries, Les Sauvagees, St. Sampsons, Guernsey (GB) GY2 4AF

(73) Assignees: Poulson Roser A/S, Fredensborg (DK); Raymond J. Evison, Guernsey, Channel Islands (GB)

( * ) Notice: Subject to any disclaimer, the term of this patent is extended or adjusted under 35 U.S.C. 154(b) by 0 days.

(21) Appl. No.: 12/384,458

(22) Filed: Apr. 6, 2009

(65) Prior Publication Data

US 2010/0257647 P1 Oct. 7, 2010

(51) Int. Cl.
*A01H 5/00* (2006.01)

(52) U.S. Cl. ..... Plt./228

(58) Field of Classification Search ..... Plt./228

See application file for complete search history.

*Primary Examiner*—Kent L Bell

(57) ABSTRACT

A new *Clematis* plant with a compact growth habit and profuse red flowers with a red and white flower centre and continuous summer flowering. The variety successfully propagates from softwood cuttings and is suitable for cultivation in commercial nursery and glasshouse culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo016'.

SUMMARY OF THE CLAIMED PLANT

The present invention constitutes a new and distinct variety of *Clematis* plant which originated from a controlled crossing between the female seed parent *Clematis* 'Bees Jubilee', and the male pollen parent, an un-named seedling.

The two parents were crossed during the summer of 1997 and the resulting seeds were planted the following winter in a controlled environment in Guernsey, Channel Islands, United Kingdom. The new variety named 'Evipo016' originated as a single seedling from the stated cross.

The new *clematis* plant may be distinguished from its female seed parent primarily by flower color. 'Bees Jubilee' has pink flowers, while 'Evipo016' has red flowers.

The new *clematis* plant may be distinguished from its male pollen parent by the following combination of characteristics:

1. The pollen parent is less compact in height than 'Evipo016'.
2. The pollent parent has pink flowers, while 'Evipo016' has red flowers.

The objective of the hybridization of this *clematis* plant was to create a new and distinct variety for commercial glasshouse and nursery culture with unique qualities such as:

1. Uniform and profuse red flowers;
2. Vigorous and compact growth, making the variety suitable for medium container culture
3. Flowers on season old and current seasons growth.
4. Consistent flower production on commercial scale.

This combination of qualities was lacking in *clematis* plants that were in commercial cultivation and the qualities have been substantially achieved in the new variety.

'Evipo016' was selected by Mogens N. Olesen and Raymond J. Evison in their *clematis* development program in the Channel Islands, United Kingdom in July 1998. Asexual reproduction of 'Evipo016' by means of vegetative cuttings and traditional layering was first performed by Mogens N. Olesen and Raymond J. Evison in the nursery during the summer of 1998. This initial and subsequent asexual propagations have demonstrated that the characteristics of 'Evipo016' are true to type and are transmitted from one generation to the next.

BRIEF DESCRIPTION OF THE DRAWING

The accompanying color illustration show as true as is reasonably possible to obtain in color photographs of this type:

1. Sheet 1 : Bloom, upper side;
2. Sheet 1 : Bloom, lower side;
3. Sheet 2 : Stem, leaves, bud at ¼ opening, bud closed;
4. Sheet 2 : Stem and leaves; and
5. Sheet 2 : Stem and juvenile foliage.

DETAILED DESCRIPTION OF THE VARIETY

Figure 1:
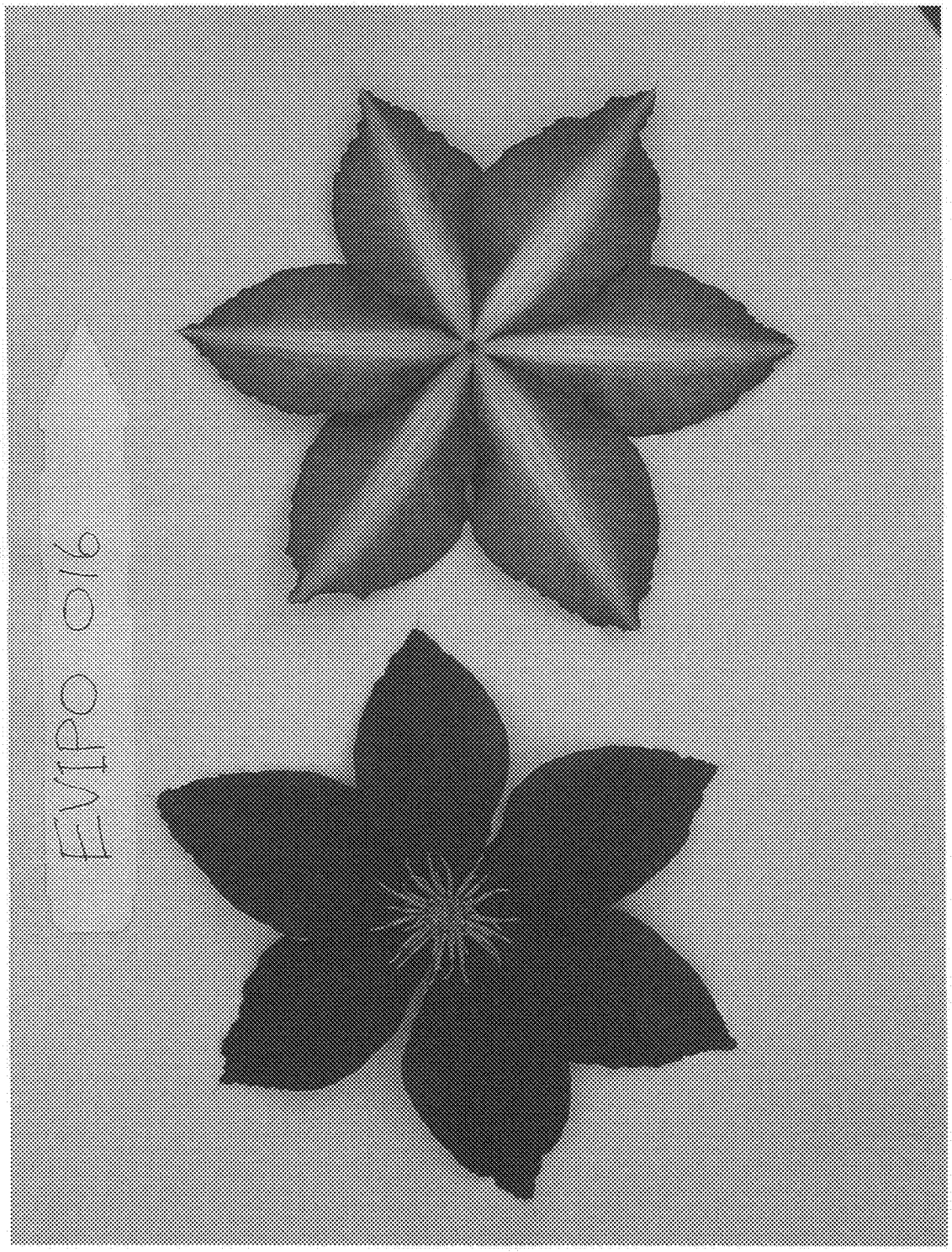

The following is a detailed description of 'Evipo016', as observed in its growth throughout the flowering period in glasshouses in the Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo002' described and illustrated in U.S. Plant Pat. No. 15,797 issued June 14, 2005 are compared to 'Evipo016' in Chart 1.

FLOWER AND FLOWER BUD

Blooming habit: Continuous. The natural flowering period is generally from March to November.

Flower bud:

*Size.*—Normally 35-60 mm in length. Bud diameter is 10-15 mm.

*Bud form.*—Lanceolate.

*Bud color.*—At ¼ opening buds are Green Group RHS No. 142B and Green Group RHS No. 145C. Margin of tepal is Red Purple Group RHS No. 70A.

Peduncle:

*Surface texture.*—Smooth pubescent.

*Length.*—On average 50-95 mm.

*Diameter.*—On average 3 mm.

*Color.*—Typically Green Group RHS No. 143C.

*Strength.*—Moderately strong.

Receptacle: Absent.

Flower arrangement:

*Location on vine.*—New and old growth.

*Borne.*—Normally in clusters of 3-5 flowers.

Flower bloom:

*Size.*—On average, flowers are 130-185 mm in diameter and 30 mm in depth.

*Profile.*—Upon opening the flowers are flat. After opening the flowers are flat with tepals reflexing, convexing slightly as flower ages.

*Fragrance.*—None.

*Lasting quality.*—Flowers normally remain 7-12 days on the plant. As a cut flower, flowers normally last up to 3-5 days.

Tepals:

*Tepal color.*—Upon opening, the upper surface is red velvet in appearance Red Group RHS No. 53A. After opening, the upper surface is Red Group RHS No. 53A with velvet appearance and fades to Red Purple Group RHS No. 71A as flower ages. Intonations of White Group RHS No. N155A observed at tepal base. Lower surface is Red Purple Group RHS No. 71A with midrib White Group RHS No. N155A.

*Quantity.*—Normally 6 tepals. Occasionally, 4 to 8 tepals observed.

*Size.*—60-95 mm in length by 30-55 mm wide.

*Shape.*—Individual tepal shape is ovate to elliptic. The tepal apex is mucronate. Mucronate tip is 3-6 mm in length. Tepal base is attenuate.

*Recurvature of tip.*—Slightly reflexed, becoming convexed as flower ages.

*Tepal cross section.*—Slightly reflexed.

*Margins.*—Entire. Undulation of margin is moderate.

*Persistence.*—Tepals drop off cleanly as flower matures.

Reproductive organs:

*Pollen.*—Quantity: Moderate. Color: Yellow Group RHS No. 4D.

*Anthers.*—Size: 6 mm in length. Color: Grey Orange RHS No. 177A. Quantity: 45-90.

*Filaments.*—Color: White Group RHS No. N155A. Base is violet blue RHS No. 92C. Length: 9 to 15 mm.

*Pistils.*—Quantity: 20-50.

*Stigmas.*—Inferior becoming Superior in location relative to the length of the filaments and the height of the anthers as the flower ages.

*Styles.*—Color: Yellow Group RHS No. 8D. Length: 12-18 mm.

Seed head characteristics:

*Size.*—40 mm in diameter at the base.

*Shape.*—The general shape of the seedhead is tear shaped with a diameter of 4 mm with elongated plumule.

PLANT

Plant form: Climbing.

Plant growth: Vigorous.

Size: Seasons growth attains 1.2 to 1.5 meters in height. Average spread is 75 cm.

Hardiness: Trials to date show the variety hardy in USDA Zones 4-9.

Stems:

*Dimensions.*—Diameter is 3 to 4 mm. Typically 60 to 70 cm from the base of the plant to the flowering portion.

*Color.*—Juvenile stems are generally Grey Brown Group RHS No. 200A. Mature stems are Greyed Orange Group RHS No. 175B.

*Internodes:.*—Cylindrical in cross section. On average, 110-170 mm between nodes.

*Surface.*—Young stems are smooth and pubulent. Mature stems are generally ribbed.

Plant foliage:

*Leaf characteristics.*—Deciduous.

*Arrangement.*—Trifoliate but also large portion of simple leaves occurring toward the upper portion of the plant. Average leaflet count is 1 to 3.

*Leaf shape.*—Leaflets and simple leaves are rounded at the base and acute at the apex. Some mature leaves have a cleft on each or one side. Otherwise, margins are entire.

*Leaf size.*—Compound leaves are normally 150 to 210 mm (1) ×140 to 190 mm (w). Simple leaves are 55 to 80 mm long and 35 to 40 mm wide. Leaflets are 60 to 80 mm long and 30 to 45 mm wide.

*Abundance.*—Generally, there are 14 leaves per 100 cm of stem.

*Leaf color.*—The upper surfaces of mature leaves and simple leaves are Green Group RHS No. 138A, while the lower surfaces are Green Group RHS No. 139D. Upper surfaces of juvenile leaves are are Green Group RHS No. 141B, while the lower surfaces are Green Group RHS No. 139C.

*Stipules.*—Absent.

*Petioles.*—Size: Normally 70 to 115 mm in length for simple and compound leaves. Texture: Smooth. Color: Greyed Purple Group RHS No. 183B. Lower surface is Yellow Green Group RHS No. 146D.

*Petioloule.*—Size: Normally 8 to 40 mm in length. Terminal petiolule. Texture: Smooth. Color: Greyed Purple Group RHS No. 183B. Leaf edge: Terminal leaflet margin is entire.

*Leaflet shape.*—Ovate and elliptic. The base of single leaves is is cordate. Tri-foliate leaves have a rounded base. Apex is normally acute.

*Margin.*—Entire. Some mature leaflets have a cleft on one or both sides.

*Surface.*—The upper side is smooth. The lower side is smooth.

*Thickness.*—Thin.

*Glossiness.*—Juvenile foliage is glossy. Mature foliage has a matte appearance.

Disease resistance: Subject to any disease that normally attacks the species. The variety is more tolerant to *clematis* wilt than some *clematis*.

Pest susceptibility: Subject to any insect pest that normally attacks the species.

We claim:

1. A new and distinct variety of *clematis* plant named 'Evipo016', substantially as described and illustrated , due to its abundant profuse red flowers with good keepability, attractive long lasting foliage and compact growth and repeatable flowering under glasshouse conditions, suitability for production from softwood cuttings in pots, durable flowers and foliage which make the variety suitable for distribution in the floral industry:

* * * * *

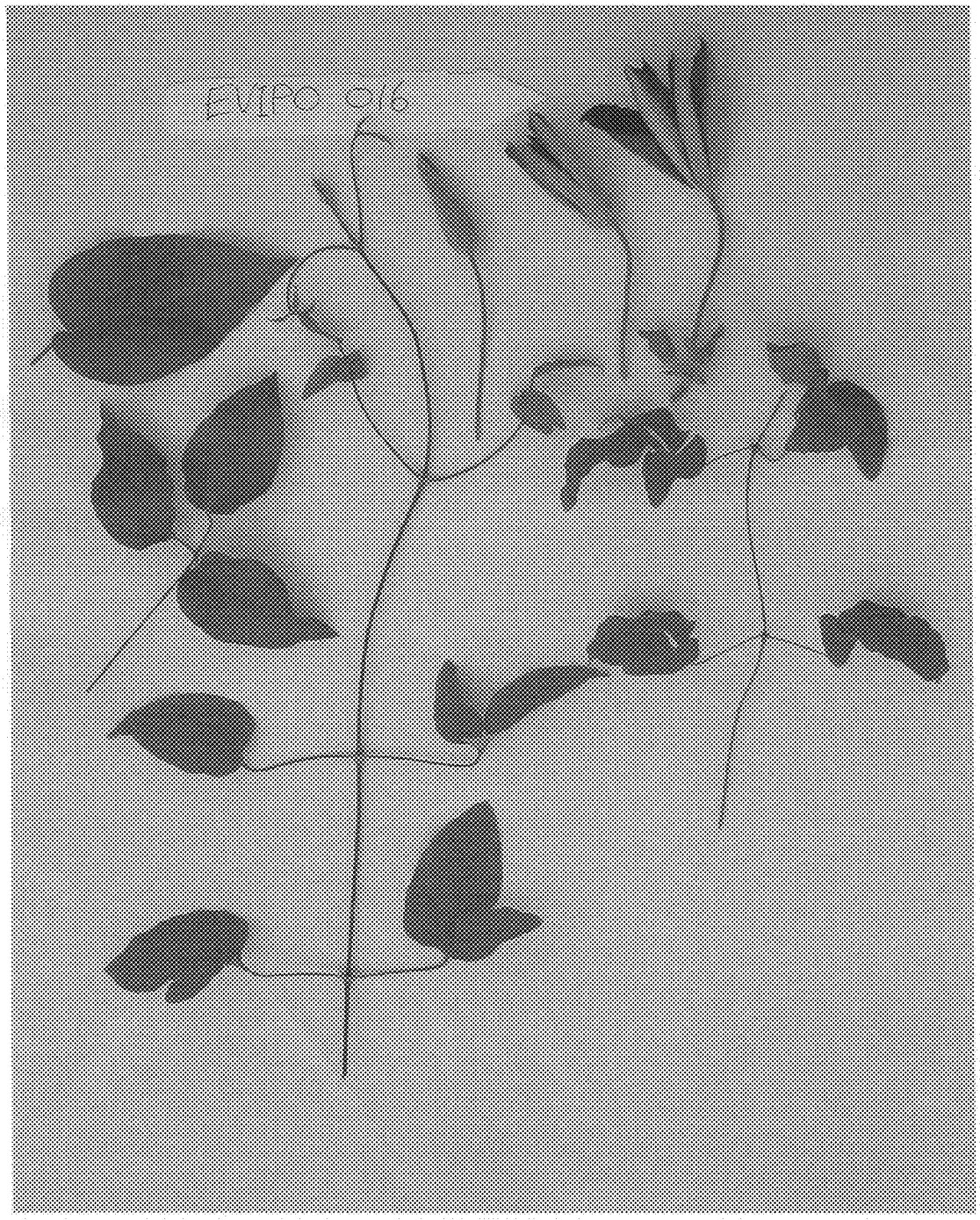
PVPO 916